United States Patent
Fago et al.

(10) Patent No.: US 10,322,228 B2
(45) Date of Patent: Jun. 18, 2019

(54) POWER INJECTOR WITH DECAY CONSTANT FUNCTIONALITY

(71) Applicant: LIEBEL-FLARSHEIM COMPANY LLC, Hazelwood, MO (US)

(72) Inventors: Frank M. Fago, Mason, OH (US); Alya Schalabi, Cologne (DE)

(73) Assignee: Liebel-Flarsheim Company LLC, Cincinnati, OH (US)

( * ) Notice: Subject to any disclaimer, the term of this patent is extended or adjusted under 35 U.S.C. 154(b) by 543 days.

(21) Appl. No.: 15/040,262

(22) Filed: Feb. 10, 2016

(65) Prior Publication Data

US 2016/0158434 A1 Jun. 9, 2016

Related U.S. Application Data

(62) Division of application No. 12/810,149, filed as application No. PCT/US2009/054101 on Aug. 18, 2009, now abandoned.

(Continued)

(51) Int. Cl.
*A61M 5/00* (2006.01)
*A61M 5/145* (2006.01)
(Continued)

(52) U.S. Cl.
CPC ............ *A61M 5/007* (2013.01); *A61B 6/032* (2013.01); *A61B 6/481* (2013.01);
(Continued)

(58) Field of Classification Search
CPC ................................ A61M 5/007; A61B 6/481
See application file for complete search history.

(56) References Cited

U.S. PATENT DOCUMENTS 5,685,844 A 11/1997 Martilla
6,055,985 A 5/2000 Bae et al.
(Continued)

FOREIGN PATENT DOCUMENTS

WO 1996/032887 A1 10/1996
WO 0064353 11/2000
(Continued)

OTHER PUBLICATIONS

Bae et al., Uniform Vascular Contrast Enhancement and Reduced Contrast Medium Volume Achieved by Using Exponentially Decelerated Contrast Material Injection Method, Radiology 2004; 231: 732-736.*

(Continued)

*Primary Examiner* — Eric D. Bertram
(74) *Attorney, Agent, or Firm* — Marsh Fischmann & Breyfogle LLP

(57) ABSTRACT

A power injector is disclosed having power injector control logic, which in turn includes a decay constant cross-reference, for instance in the form of a data structure. Flow rate decay constant information may be stored by the decay constant cross-reference. A decay constant, which may be used by the power injector to generate an exponentially decaying flow rate for an injection, may be stored in the decay constant cross-reference in conjunction with a particular imaging unit. The decay constant cross-reference may be searched by entering a model or module number of an imaging unit to identify the corresponding flow rate decay constant to be used by the power injector.

19 Claims, 11 Drawing Sheets

Related U.S. Application Data

(60) Provisional application No. 61/090,911, filed on Aug. 22, 2008.

(51) Int. Cl.
*G06F 19/00* (2018.01)
*A61B 6/03* (2006.01)
*A61B 6/00* (2006.01)
*A61M 5/142* (2006.01)

(52) U.S. Cl.
CPC ..... *A61M 5/14546* (2013.01); *G06F 19/3468* (2013.01); *A61B 6/548* (2013.01); *A61M 2005/14208* (2013.01); *A61M 2005/14553* (2013.01); *G06F 19/321* (2013.01)

(56) References Cited

U.S. PATENT DOCUMENTS

| | | |
|---|---|---|
| 6,470,889 B1 | 10/2002 | Bae et al. |
| 6,540,152 B2 | 4/2003 | Holm et al. |
| 6,578,773 B2 | 6/2003 | Holm et al. |
| 6,635,030 B1 | 10/2003 | Bae et al. |
| 7,672,711 B2 | 3/2010 | Haras et al. |
| 7,925,330 B2 | 4/2011 | Kalafut et al. |
| 7,967,778 B2 | 6/2011 | Nemoto et al. |
| 8,016,744 B2 | 9/2011 | Dlugos et al. |
| 8,066,629 B2 | 11/2011 | Dlugos |
| 2004/0064040 A1 | 4/2004 | Masuda et al. |
| 2004/0199076 A1 | 10/2004 | Nemoto |
| 2005/0228272 A1 | 10/2005 | Yu |
| 2006/0211912 A1 | 9/2006 | Dlugos et al. |
| 2006/0211913 A1 | 9/2006 | Dlugos et al. |
| 2007/0219496 A1 | 9/2007 | Kamen et al. |
| 2007/0228071 A1 | 10/2007 | Kamen et al. |
| 2007/0235083 A1* | 10/2007 | Dlugos ............... A61F 5/0003 137/223 |
| 2007/0255135 A1 | 11/2007 | Kalafut et al. |
| 2011/0201867 A1 | 8/2011 | Wagner |
| 2013/0184575 A1 | 7/2013 | Nemoto |

FOREIGN PATENT DOCUMENTS

| | | |
|---|---|---|
| WO | 2005/104697 A2 | 11/2005 |
| WO | 2007/039838 A2 | 4/2007 |
| WO | 2008/085421 A2 | 7/2008 |

OTHER PUBLICATIONS

Bae et al., "Uniform Vascular Contrast Enhancement and Reduced Contrast Medium Volume Achieved by Using Exponentially Decelerated Contrast Media Injection Method," Radiology Jun. 2004; vol. 231, No. 3, pp. 732-736.

* cited by examiner

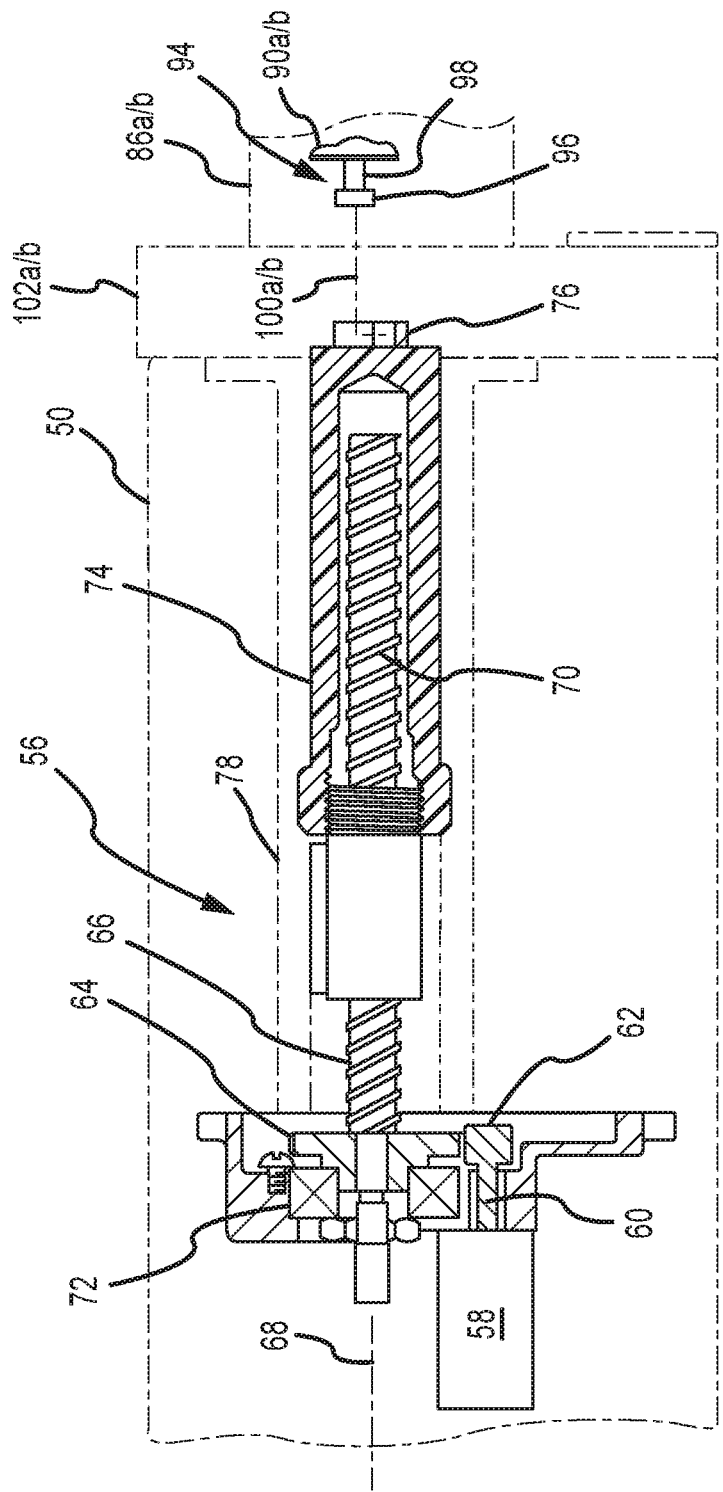

POWER INJECTOR WITH DECAY CONSTANT FUNCTIONALITY

CROSS-REFERENCE TO RELATED APPLICATIONS

This application is a divisional application of U.S. patent application Ser. No. 12/810,149, filed on Jun. 23, 2010 (now abandoned), which is a U.S. National Stage of PCT/US2009/054101, filed on Aug. 18, 2009, which claims the benefit of U.S. Provisional Patent Application No. 61/090,911, filed on Aug. 22, 2008. The entire disclosure of each patent application set forth in this Cross-Reference to Related Applications section is incorporated by reference.

FIELD OF THE INVENTION

The present invention generally relates to the field of power injectors and, more particularly, to a power injector configured to provide an injection on an exponentially decaying flow rate basis.

BACKGROUND

Various medical procedures require that one or more medical fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe driver that is incorporated into the powerhead, such that operation of the syringe driver axially advances the associated syringe plunger inside and relative to a barrel of the syringe. One typical syringe driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

Contrast media may be injected by a power injector into a patient's heart for an imaging operation, such as for a computed tomography angiogram. In an attempt to have the enhancement levels of the right and left sides of the patient's heart be more uniform, where this enhancement is provided by a contrast media injection, power injectors have been configured to use an injection protocol that in turn utilizes a flow rate decay constant. Such a flow rate decay constant provides an exponentially decaying flow rate injection.

SUMMARY

First and second aspects of the present invention are each embodied by a power injector, which includes a syringe plunger driver, a syringe, power injector control logic, and data storage. The syringe plunger driver includes a motorized drive source. The syringe includes a syringe plunger, where the syringe plunger driver interacts with the syringe plunger to move the same in at least one direction. The power injector control logic includes an injection protocol, which in turn utilizes a flow rate decay constant. The data storage is accessible by the power injector control logic. In the case of the first aspect, the data storage includes a plurality of data entries, where each data entry includes a flow rate decay constant value. In the case of the second aspect of the present invention, each data entry includes an imaging device identifier and an associated flow rate decay constant value.

A number of feature refinements and additional features are separately applicable to each of the first and second aspects of the present invention. These feature refinements and additional features may be used individually or in any combination. The following discussion is separately applicable to each of the first and second aspects, up to the start of the discussion of a third aspect of the present invention. The power injector may include a display or graphical user interface. A first output may be presented on this display or graphical user interface, where this first output is in the form of a listing of at least some of the data entries. In one embodiment, this first output presents a model or a model identifier for an imaging unit (e.g., a CT scanner), along with an associated flow rate decay constant value (e.g., in the form of a drop down menu).

The power injector may be configured such that the noted data storage is searchable in any appropriate manner. In one embodiment, a user is allowed to enter information regarding an imaging unit that is to be used in combination with the power injector for an imaging operation, and the noted data storage may be searched to attempt to identify such an imaging unit and its corresponding flow rate decay constant. Regardless of how information is obtained on a flow rate decay constant value for an associated imaging unit, the power injector may be configured to allow this flow rate decay constant value to be input in any appropriate manner, such as by any appropriate data input device operatively interconnected with the power injector control logic (e.g., a keyboard, a mouse, a touch screen display, a soft key display, a touch pad, a track ball, or the like).

A third aspect of the present invention is embodied by a power injector. This power injector includes a syringe plunger driver, a syringe, and power injector control logic. The syringe plunger driver includes a motorized drive source. The syringe includes a syringe plunger, where the syringe plunger driver interacts with the syringe plunger to move the same at least one direction. The power injector control logic includes an injection protocol, which in turn utilizes a flow rate decay constant. The power injector control logic further includes decay constant determination logic.

A number of feature refinements and additional features are applicable to the third aspect of the present invention. These feature refinements and additional features may be used individually or in any combination. The following discussion is applicable to the third aspect, up to the start of the discussion of a fourth aspect of the present invention. In one embodiment, the decay constant determination logic includes a test injection protocol. Execution of this test injection protocol may be used to acquire information such that a value may be derived for a flow rate decay constant to be used in a subsequent imaging operation involving the power injector.

The decay constant determination logic may utilize an acquisition time variable. A prompt may be utilized for inputting a value for this acquisition time variable. In one embodiment, an average value is input for the acquisition time variable (e.g. based upon a priori knowledge from operation of an imaging unit to be used in combination with the power injector to acquire a patient image). In one embodiment, a patient-specific value is input for the acquisition time variable (e.g., dividing the number of patient heartbeats required for an imaging unit (to be used in combination with the power injector) to acquire a patient image, divided by the number of patient heartbeats per unit of time).

The decay constant determination logic may utilize an enhancement level variable. A prompt may be utilized for inputting a value for this enhancement level variable. The value for the enhancement level variable may be selected/determined by an operator of an imaging system that is utilizing the power injector. This value may be expressed as a percentage for the case where the patient image to be acquired is of a heart. In this regard, the value for the enhancement level variable may be a desired enhancement level for the left side of the patient's heart, expressed as a percentage of the enhancement level on the right side of the patient's heart.

The decay constant determination logic may utilize a time delay variable. A prompt may be utilized for inputting a value for this time delay variable, and in any case a patient-specific value may be input for the time delay variable. In one embodiment, the value for the time delay variable is the amount of time required from the start of an injection (pursuant to the test injection protocol) until the input value for the enhancement level variable is realized (e.g., until the desired enhancement level is reached on the left side of the patient's heart).

In one embodiment, the decay constant determination logic utilizes each of the noted acquisition time, enhancement level, and time delay variables. A decay constant value generated by the decay constant determination logic may be equal to the time delay variable, minus one-half of the acquisition time variable, divided into the natural logarithm of the enhancement level variable.

A fourth aspect of the present invention is embodied by a method of acquiring a medical image using an imaging system, where this imaging system includes a power injector and an imaging unit. A search may be conducted for a value to be used for a flow rate decay constant, where this search is based upon a model or model number of the imaging unit to be used for the imaging operation. A value is input for the flow rate decay constant, and that is associated with the model of the particular imaging unit to be used for the imaging operation. An injection is then delivered by operation of the power injector using the inputted value for the flow rate decay constant.

A number of feature refinements and additional features are applicable to the fourth aspect of the present invention. These feature refinements and additional features may be used individually or in any combination. The following discussion is applicable to the third aspect, up to the start of the discussion of a fifth aspect of the present invention. The injection associated with the fourth aspect may facilitate acquisition of a patient image (e.g., an image of a patient's heart). In one embodiment, the imaging unit is operated during and/or after the injection to acquire a patient image for flow rate constant determination purposes. Although the fourth aspect may be used for any imaging application, in one embodiment the imaging operation is for purposes of a computed tomography angiogram.

A prompt may be provided for entry of a value of the flow rate of decay constant to be used for an injection provided by operation of the power injector. In one embodiment, this prompt is presented on a display associated with the power injector (e.g., a display on a powerhead of the power injector; on a remote console associated with the power injector). Any appropriate data entry vice may be utilized to input a desired value for the flow rate decay constant, including without limitation a keyboard, a mouse, a touch screen display, a soft key display, a touch pad, a track ball, or the like.

The search for a value for the flow rate decay constant may include accessing or consulting a cross-reference of imaging unit model numbers to flow rate decay constants. This cross-reference may be stored on and/or incorporated by power injector control logic utilized by the power injector. However, this cross-reference could be in any appropriate form (e.g., hard copy) and stored at any appropriate location.

Another option for the search regarding a value for the flow rate decay constant may entail retrieving a value from memory associated with the power injector. The search may entail accessing a lookup table incorporated by the power injector. Yet another option would be to use the Internet for the search. Any appropriate search may be undertaken to identify a value for the flow rate decay constant to be used for an ejection provided by the power injector for purposes of undertaking an imaging operation.

A fifth aspect of the present invention is embodied by a method for acquiring a medical image using an imaging system, where this imaging system includes a power injector and an imaging unit. A first injection is delivered to a patient. This first injection is monitored, and a flow rate decay constant is derived based at least in part from this monitoring of the first injection. Thereafter, a second injection is delivered to the patient and which uses the derived flow rate decay constant.

A number of feature refinements and additional features are applicable to the fifth aspect of the present invention. These feature refinements and additional features may be used individually or in any combination. The following discussion is applicable to at least this fifth aspect of the present invention. The first injection may utilize any appropriate fluid or combination of fluids (e.g., contrast media, alone or in combination with saline), may inject any appropriate fluid volume (e.g., no more than at least generally about 15 mL in one embodiment; no more than at least generally about 10 mL in one embodiment; within a range from at least generally about 5 mL to at least generally about 15 mL (inclusive) in one embodiment), and may utilize any appropriate flow rate (e.g., a constant flow rate within a range of at least generally about 3-6 mL/second in one embodiment; a constant flow rate within a range of at least generally about 4-5 mL/second in one embodiment; a constant flow rate of no more than at least generally about 6 mL/second in one embodiment). As this first injection may be used at least in part to acquire a value for the flow rate decay constant, it may be characterized as a test injection.

The monitoring of the first injection may be for purposes of acquiring data to be used in the derivation of a value for the flow rate decay constant. As the first injection may entail an injection of a fluid into the patient, the monitoring of the first injection may be characterized as acquiring this patient-specific data. The monitoring of the first injection may entail monitoring an image intensity of at least part of the heart of the patient.

In one embodiment, the fifth aspect is directed to executing a computed tomography angiogram. In this and for any other appropriate case, the monitoring for purposes of the first injection may entail monitoring an image intensity of the left side of the patient's heart as a result of the first injection. This monitoring may also include determining the amount of time required for the image intensity of the left side of the patient's heart (from the first injection) to reach a predetermined level (e.g., an input value for an enhancement level variable in accordance with the above-noted third aspect), and which may be expressed as a percentage of the intensity of the right side of the patient's heart (from the first injection). The target enhancement level may be at least generally about 50% in one embodiment, and may be at least generally about 25% in another embodiment (e.g., the amount of time required for the image intensity of the left side of the patient's heart to reach 50% (in one embodiment) or 25% (in another embodiment) of the image intensity of the right side of the patient's heart).

One or more prompts may be issued in relation to deriving a value for the flow rate decay constant. Each such prompt may be issued at any appropriate location and in any appropriate manner. Any appropriate data entry vice may be utilized to input any appropriate value in relation to any such prompt, including without limitation a keyboard, a mouse, a touch screen display, a soft key display, a touch pad, a track ball, or the like. Prompts may be issued in relation to a value for one or more of an enhancement level variable, an acquisition time variable, and a time delay variable. A value for the flow rate decay constant may be derived for purposes of the fifth aspect in the manner discussed above in relation to the third aspect.

A number of feature refinements and additional features are separately applicable to each of the above-noted first through the fifth aspects of the present invention as well. These feature refinements and additional features may be used individually or in any combination in relation to each of the first through the fifth aspects. Initially, any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that the power injector includes "a syringe" alone does not mean that the power injector includes only a single "syringe"). Moreover, any failure to use phrases such as "at least one" also does not limit the corresponding feature to the singular (e.g., indicating that the power injector includes "a syringe" versus "at least one syringe" alone does not mean that the power injector includes only a single "syringe"). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical; indicating that a maximum fluid volume is at least generally about 15 mL encompasses the maximum fluid volume being 15 mL).

Any "logic" that may be utilized by any of the various aspects of the present invention may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

The power injector may be of any appropriate size, shape, configuration, and/or type. The power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

The power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with the power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., a medical tubing set), where this conduit is fluidly interconnected with the syringe in any appropriate manner and directs fluid to a desired location (e.g., to a catheter that is inserted into a patient, for instance for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

BRIEF DESCRIPTION OF THE FIGURES

FIG. 2C is a schematic of one embodiment of a syringe plunger drive assembly used by the power injector of FIG. 2A.

DETAILED DESCRIPTION

Figure 1:
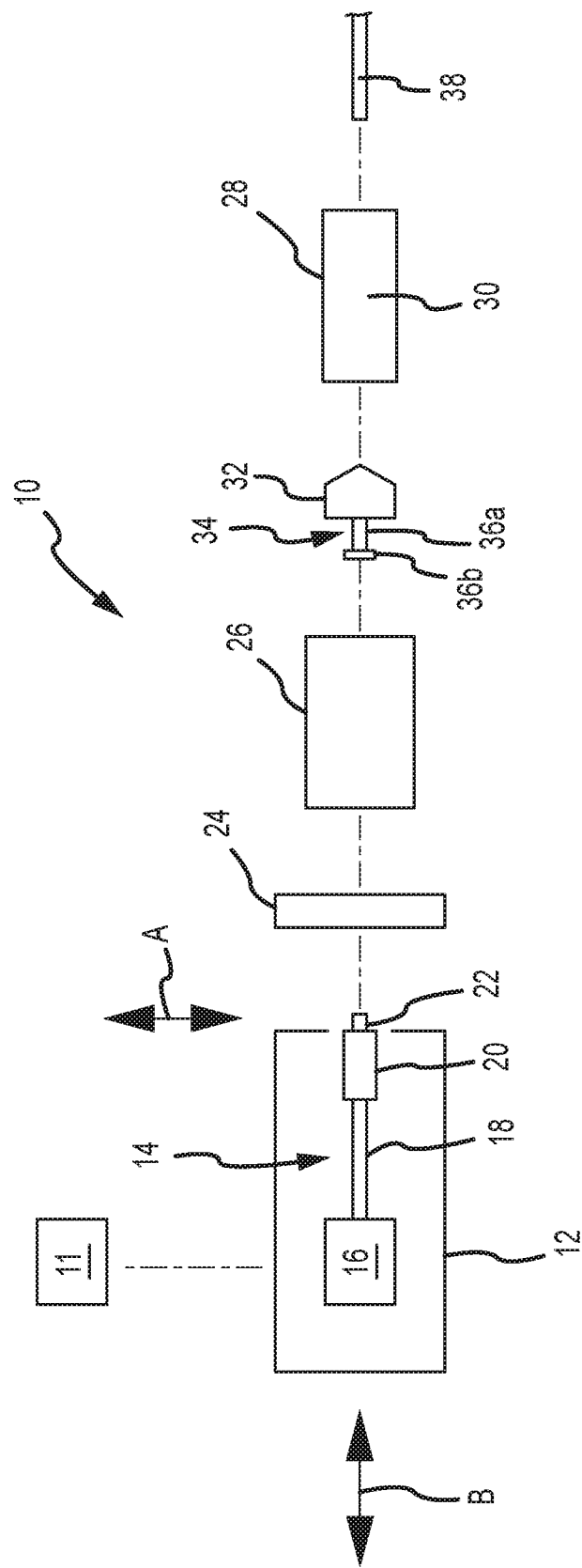
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
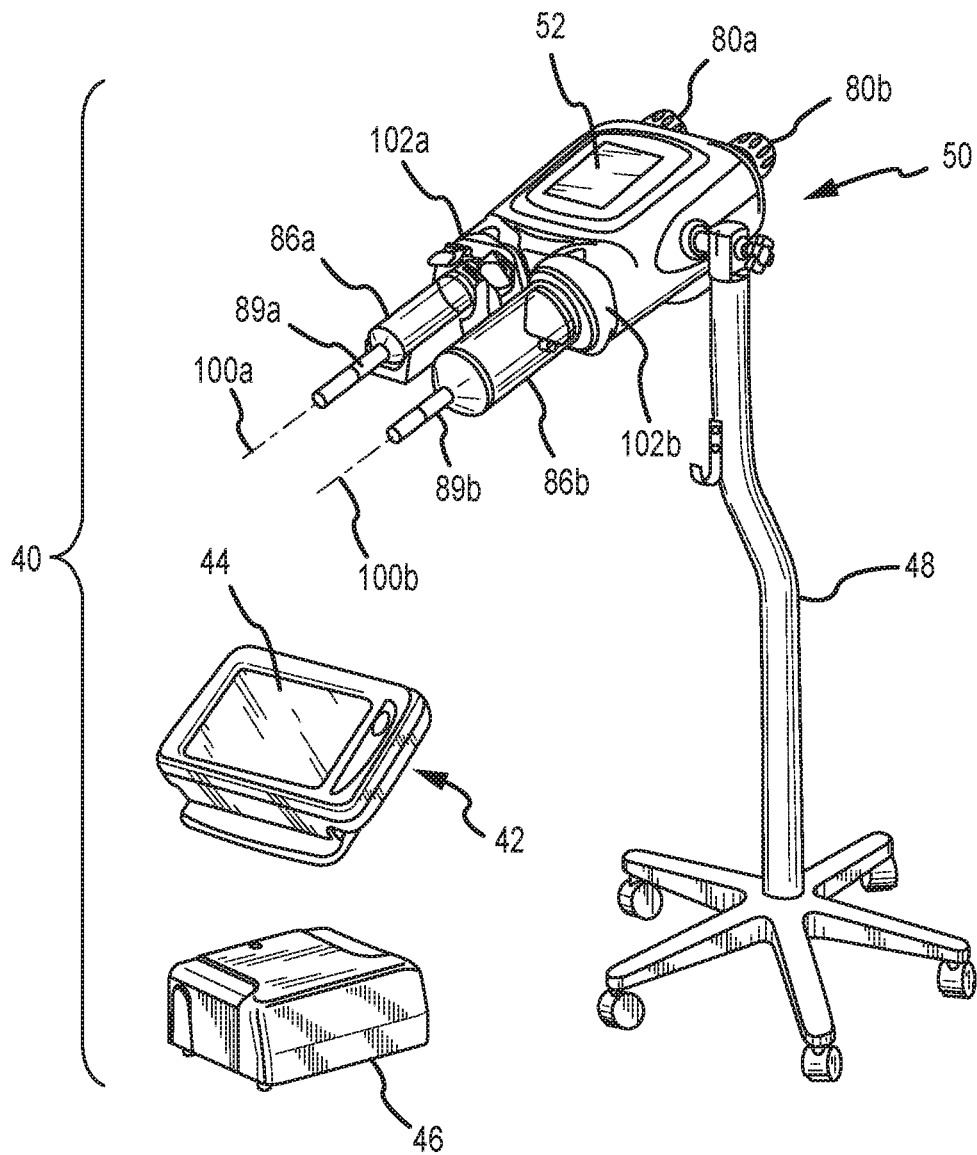
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
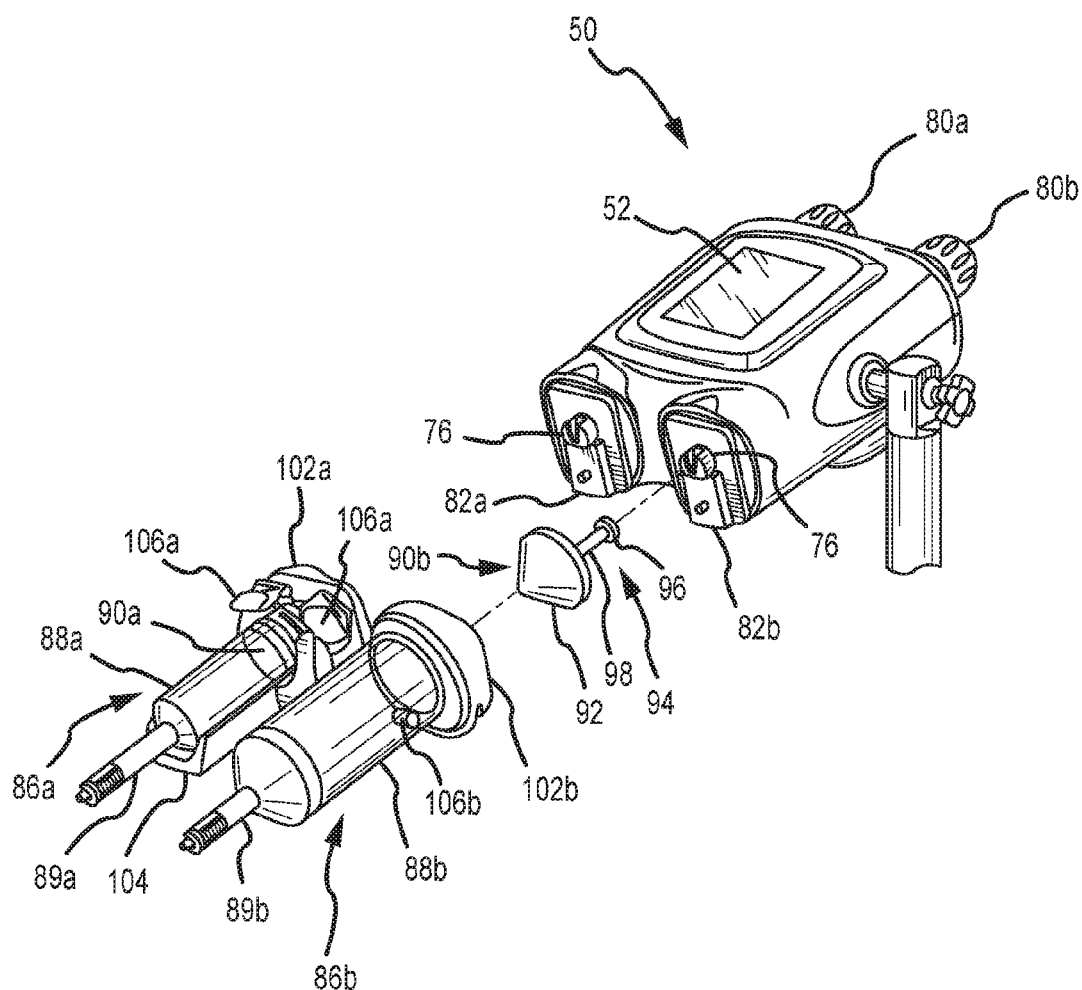
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74 (FIG. 2C), which are each part of a syringe plunger drive assembly or syringe plunger driver 56 (FIG. 2C) for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 (FIG. 2C) may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 86*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of handles 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74 (FIG. 2C), which are each part of a syringe plunger drive assembly 56 for the syringe 86*b*, is positioned in proximity to the faceplate 102*b* when mounted to the powerhead 50. Details regarding the syringe plunger drive assembly 56 again will be discussed in more detail below in relation to FIG. 2C. Generally, the ram coupler 76 may be coupled with the syringe plunger 90*b* of the syringe 86*b*, and the ram coupler 76 and ram 74 (FIG. 2C) may be moved relative to the powerhead 50 to move the syringe plunger 90*b* along the axis 100*b* (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radio-pharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
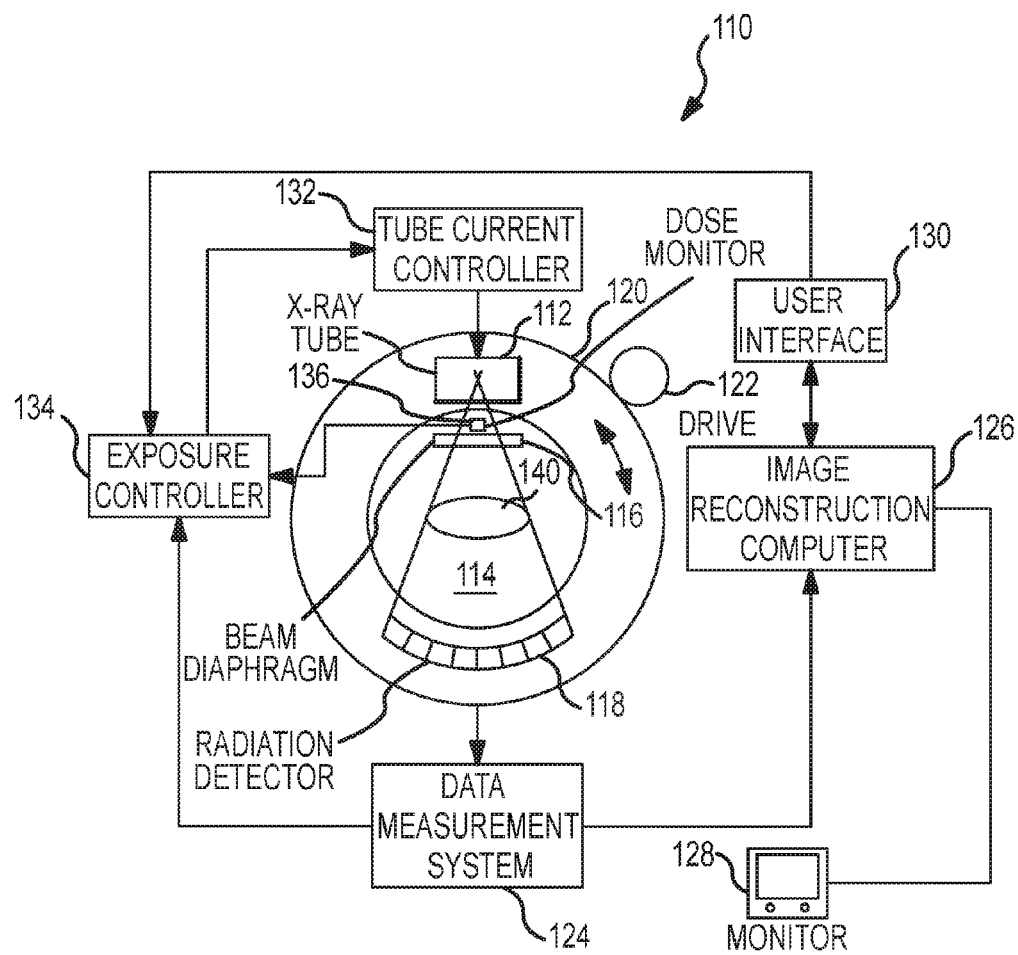
FIG. 3 is a functional schematic of a CT scanner.

FIG. 3 illustrates a functional schematic of a computed tomography or CT scanner 110. The CT scanner 110 includes an X-ray tube 112 that emits an X-ray beam 114. The X-ray beam 114 is gated by a beam diaphragm 116, proceeds through a patient 140, and is incident on a radiation detector 118. The X-rays incident on the radiation detector 118 are attenuated by the patient 140. The radiation detector 118 generates electrical signals corresponding to the attenuated X-ray incident thereon.

The X-ray tube 112 and the radiation detector 118 are mounted on a gantry 120 which may be rotated by a drive 122. The X-ray beam 114 is therefore caused to rotate around the patient 140, so that a series of projections are made, each being typically obtained at a different projection angle. Each projection has a dataset of the aforementioned electrical signals associated therewith. The dataset from each projection is supplied from the radiation detector 118 to a data measurement system 124 for collection and editing. Moreover, these datasets are supplied from the data measurement system 124 to an image reconstruction computer 126, which in turn constructs a CT image of the patient 140 from the projection data in a known manner. This image is displayed on a monitor 128 connected to the image reconstruction computer 126.

The CT scanner 110 also includes a user interface 130 that is connected to the image reconstruction computer 126. The image reconstruction computer 126 may also serve as an overall system control computer and thereby may include connections in a known manner (not shown) to various components, such as the drive 122, a voltage supply for the X-ray tube 112 and that is embodied in a tube current controller 132, and the beam diaphragm 116. Alternatively, a separate control computer can be used for these purposes.

The CT scanner 110 may also include an exposure controller 134 and a dose monitor 136. The exposure controller 134 receives a signal from the dose monitor 136, which is disposed in the X-ray beam 114, indicating the intensity of the X-rays before being attenuated by the patient 140. The exposure controller 134 also receives signals from the data measurement system 124, representing the attenuated X-rays, so that the exposure controller 134 can calculate an attenuation profile of the patient 140 from the signals from the dose monitor 136 and the data measurement system 124.

Figure 4:
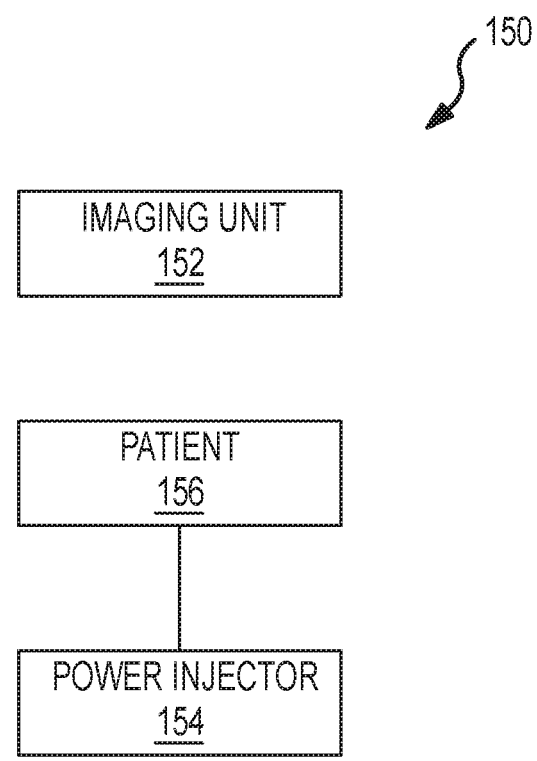
FIG. 4 is a functional schematic of one embodiment of an imaging system.

One embodiment of an imaging system is illustrated in FIG. 4 and is identified by reference numeral 150. The imaging system 150 includes an imaging unit 152 and a power injector 154. The imaging unit 152 may be of any appropriate size, shape, configuration, and/or type, and its image-acquisition functionality may utilize any appropriate technology or combination of technologies. In one embodiment, the imaging unit 152 is in the form of a computed tomography scanner, for instance the CT scanner 110 shown in FIG. 3.

The power injector 154 of the imaging system 150 also may be of any appropriate size, shape, configuration, and/or type, for instance in the form of the power injectors 10, 40 discussed above. In any case, the power injector 154 is fluidly interconnected with a patient 156 in any appropriate manner (e.g., via an appropriate tubing set). One or more fluids may be injected into the patient 156 for purposes of acquiring an image of the patient 156 (e.g., a "patient image") through operation of the imaging unit 152. Any appropriate patient image may be acquired by the imaging system 150. In one embodiment, the patient image is in the form of a computed tomography angiogram or CTA—an image of the heart of the patient.

Figure 5:
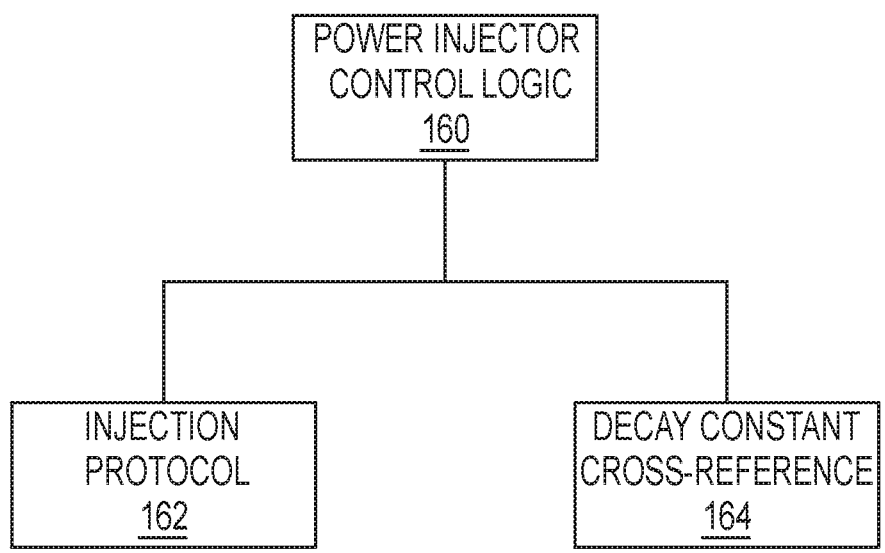
FIG. 5 is a functional schematic of one embodiment of power injector control logic that may be used by the power injector of the imaging system of FIG. 4.

The power injector 154 from the imaging system 150 of FIG. 4 may utilize power injector control logic to control one or more aspects of its operation. One representative embodiment of such power injector control logic is illustrated in FIG. 5 and is identified by reference numeral 160. The power injector control logic 160 may be configured to include one or more injection protocols 162 and a decay constant cross-reference 164. Each injection protocol 162 may utilize one or more fluids of any appropriate type (e.g., contrast media, saline), may include one or more phases, or both. Each phase may be defined as a delivery (e.g., for injection) of a predefined quantity of a predefined fluid in a predefined manner (e.g., one or more fixed flow rates, one or more variable flow rates, or a combination thereof). One or more of the injection protocols 162 may provide an exponentially decaying flow rate injection that is intended to optimize usage of contrast media, to provide a desired level/manner of enhancement of a region of interest of the patient 156 to be imaged, or both. Any appropriate number of the injection protocols 162 of the power injector control logic 160 may provide an exponentially decaying flow rate injection (e.g., not all of the injection protocols 162 of the power injector control logic 160 need to be configured to provide an exponentially decaying flow rate injection, although such could be the case). In one embodiment, at least one injection protocol 162 provides an exponentially decaying flow rate injection, while at least one injection protocol 162 does not provide such an exponentially decaying flow rate injection.

The decay constant cross-reference 164 of the power injector control logic 160 may store flow rate decay constant information (to provide the above-noted exponentially decaying flow rate injection) on an imaging unit 152 model or model number basis. The decay constant cross-reference 164 may be of any appropriate configuration to associate a particular model or model number of an imaging unit 152 with a particular flow rate decay constant. The flow rate decay constant for a particular model of imaging unit 152 may be determined or established in any appropriate manner (e.g., empirically). Any number of imaging unit 152 model/flow rate decay constant pairs may be stored in the decay constant cross-reference 164. Data for the decay constant cross-reference 164 may be stored in any appropriate manner (e.g., any appropriate data structure or data storage technique may be utilized for purposes of the decay constant cross-reference 164).

Different models of imaging units 152 may benefit in at least some respect from executing an injection protocol 162 using different flow rate decay constants. Any appropriate way may be utilized by a power injector 154 (that incorporates the power injector control logic 160 of FIG. 5) in relation to retrieving a flow rate decay constant for a particular model of imaging unit 152 from the decay constant cross-reference 164. In one embodiment, the decay constant cross-reference 164 may be searched by entering a model, model number, or some other identifier for an imaging unit 152 that is to be used to acquire a patient image. In another embodiment, the power injector 154 includes a decay constant cross-reference 164 in the form of a drop-down menu or the like that lists a plurality of model or model numbers of imaging units 152, along with their associated flow rate decay constant. A user may then simply scroll through this drop-down menu.

Figure 6:
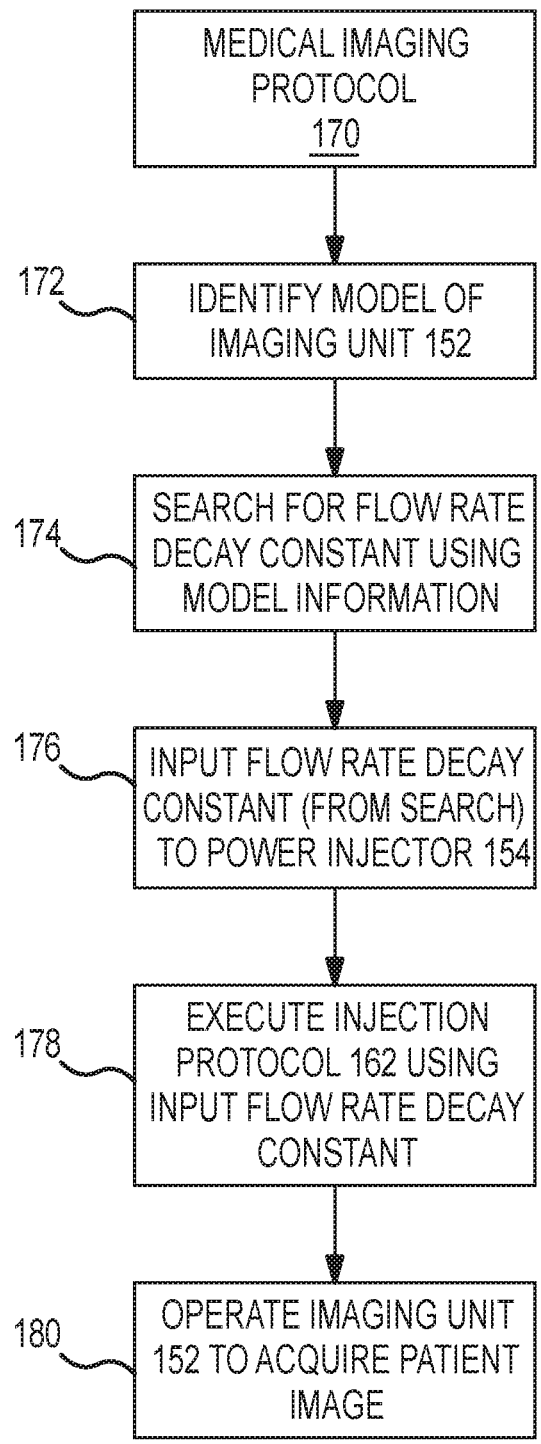
FIG. 6 is one embodiment of a medical imaging protocol that may be used by the power injector control logic of FIG. 5.

One embodiment of a medical imaging protocol is illustrated in FIG. 6, is identified by reference numeral 170, and may be utilized by the power injector control logic 160 of FIG. 5. FIG. 6 will be described for the case of the power injector control logic 160 being used by the power injector 154 from the imaging system 150 of FIG. 4. The medical imaging protocol 170 includes identifying a model or model number of an imaging unit 152 (FIG. 4) that is to be used to acquire a patient image in accordance with step 172. A search is undertaken via step 174 to identify a flow rate decay constant from the model or model number information provided through execution of step 172. Step 174 may utilize the decay constant cross-reference 164 from the power injector control logic 160 of FIG. 5. However, any appropriate search may be utilized for purposes of step 174, for instance using the Internet and an appropriate search engine (e.g., inputting a model number of an imaging unit 152 in an appropriate search engine to identify an associated flow rate decay constant).

A flow rate decay constant, identified from the search of step 174, may be input to the power injector 154 (FIG. 4) through execution of step 176 of the medical imaging protocol 170 of FIG. 6. This flow rate decay constant may be input to the power injector 154 in any appropriate manner, for instance through a setup screen of the power injector 154 (FIG. 4) using any appropriate data entry device or any combination of data entry devices. In any case and in accordance with step 178 of the medical imaging protocol 170, an injection protocol 162 is executed using this input flow rate decay constant. The imaging unit 152 (FIG. 4) may be operated to acquire a patient image pursuant to step 180 (e.g., for a computed tomography angiogram). The imaging unit 152 may acquire one or more patient images using the injection protocol 162 from step 178. The imaging unit 152 could also acquire one or more additional patient images using one or more other injection protocols 162 (other than the protocol 162 associated with step 178).

Figure 7:
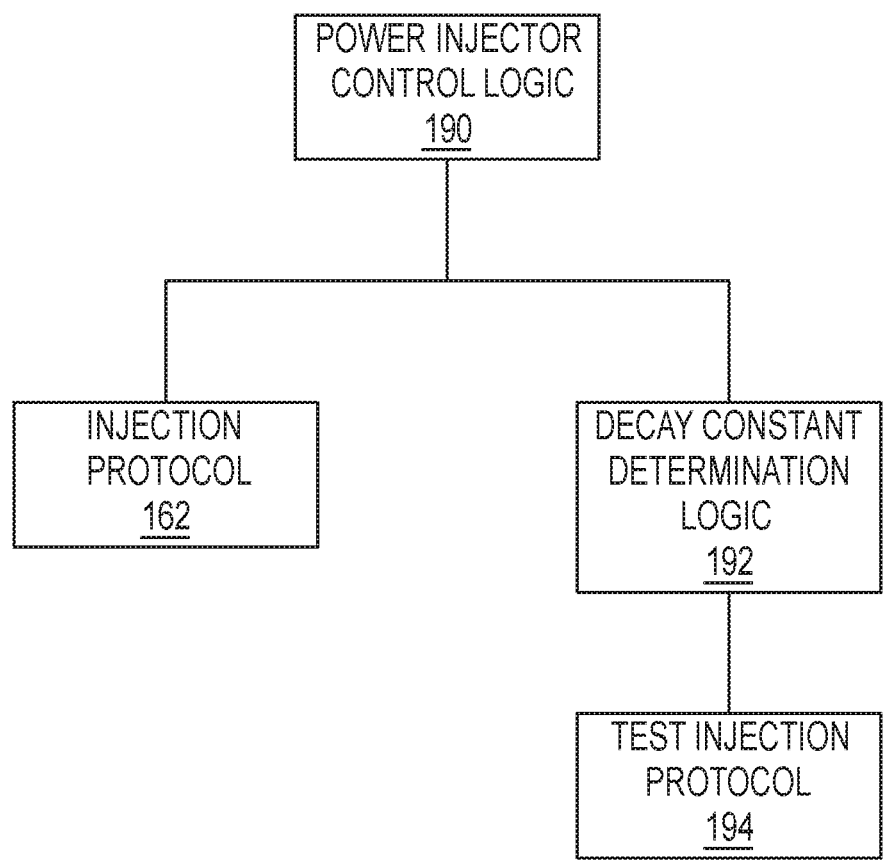
FIG. 7 is a functional schematic of another embodiment of power injector control logic that may be used by the power injector of the imaging system of FIG. 4.

Another embodiment of power injector control logic is illustrated in FIG. 7, is identified by reference numeral 190, and may be utilized by the power injector 154 from the imaging system 150 of FIG. 4. The power injector control logic 190 includes one or more of the above-noted injection protocols 162 in the same manner as the power injector control logic 160 of FIG. 5. Another component or functionality of the power injector control logic 190 of FIG. 7 is a decay constant determination protocol or logic 192. This decay constant determination logic 192 may utilize data acquired through execution of a test injection protocol 194, that may also part of the power injector control logic 190. In one embodiment, the decay constant determination logic 192 uses data acquired from execution of a test injection protocol 194 to derive or calculate a flow rate decay constant to be used by an injection protocol 162 to facilitate acquisition of a patient image (e.g., using the imaging system 150 of FIG. 4).

Figure 8:
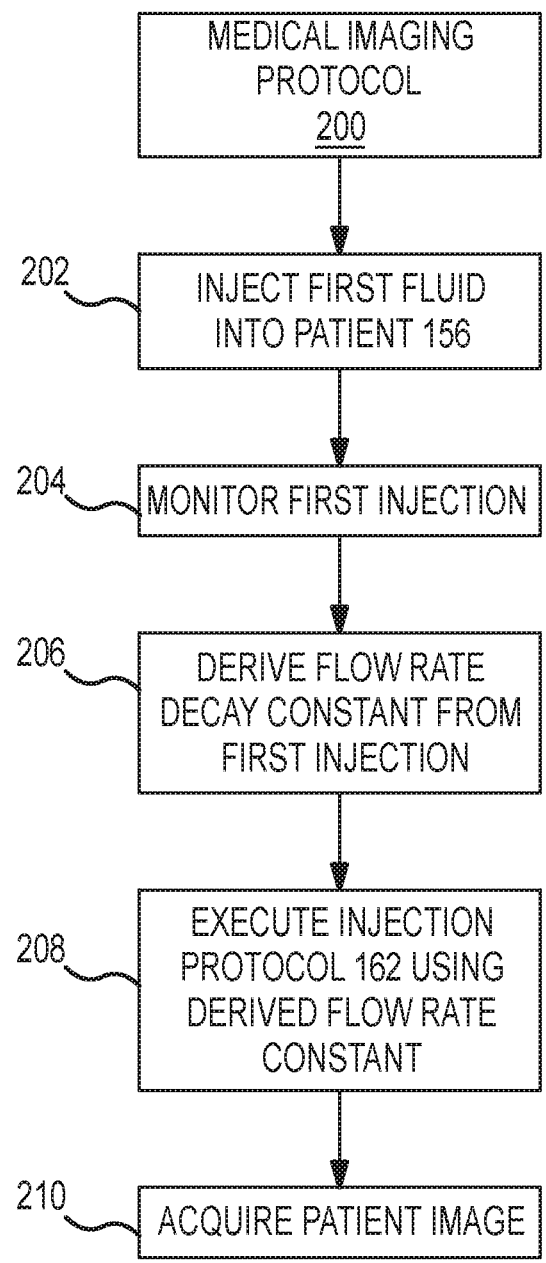
FIG. 8 is one embodiment of a medical imaging protocol that may be used by the power injector control logic of FIG. 7.

A functional schematic of one embodiment of a medical imaging protocol 200 is illustrated in FIG. 8, and may be used by the imaging system 150 of FIG. 4 when incorporating the power injector control logic 190 of FIG. 7. The medical imaging protocol 200 includes injecting a first fluid into a patient 156 (FIG. 4) through execution of step 202. In one embodiment, this first fluid is contrast media. Step 202 may be referred to as a "first injection." This first injection may utilize any appropriate fluid or combination of fluids (e.g., contrast media, alone or in combination with saline), may inject any appropriate fluid volume (e.g., no more than at least generally about 15 mL in one embodiment; no more than at least generally about 10 mL in one embodiment; within a range at least generally from about 5 mL to at least generally about 15 mL (inclusive) in one embodiment), and may utilize any appropriate flow rate (e.g., a constant flow rate within a range of at least generally about 3-6 mL/second in one embodiment; a constant flow rate within a range of at least generally about 4-5 mL/second in one embodiment; a constant flow rate of no more than at least generally about 6 mL/second in one embodiment).

The above-noted first injection associated with step 202 of the protocol 200 may be monitored in at least some manner pursuant to step 204. A flow rate decay constant is derived from the first injection (step 202) in accordance with step 206, for instance using data acquired from the first injection through execution of step 204. Although the power injector 154 (FIG. 4) could be used for this derivation, any appropriate way of executing the derivation may be used for step 206 (e.g., a hand-calculation, where the result(s) are subsequently manually input to the power injector 154). An injection protocol 162 is then executed by the power injector 154 (FIG. 4) pursuant to step 208 and using the flow rate decay constant from step 206. A patient image is acquired through execution of step 210. In one embodiment, the patient image of step 210 is for purposes of a computed tomography angiogram of a heart. As in the case of the medical imaging protocol 170 of FIG. 6, one or more patient images may also be acquired using one or more injection protocols 162 other than that associated with step 208.

Figure 9:
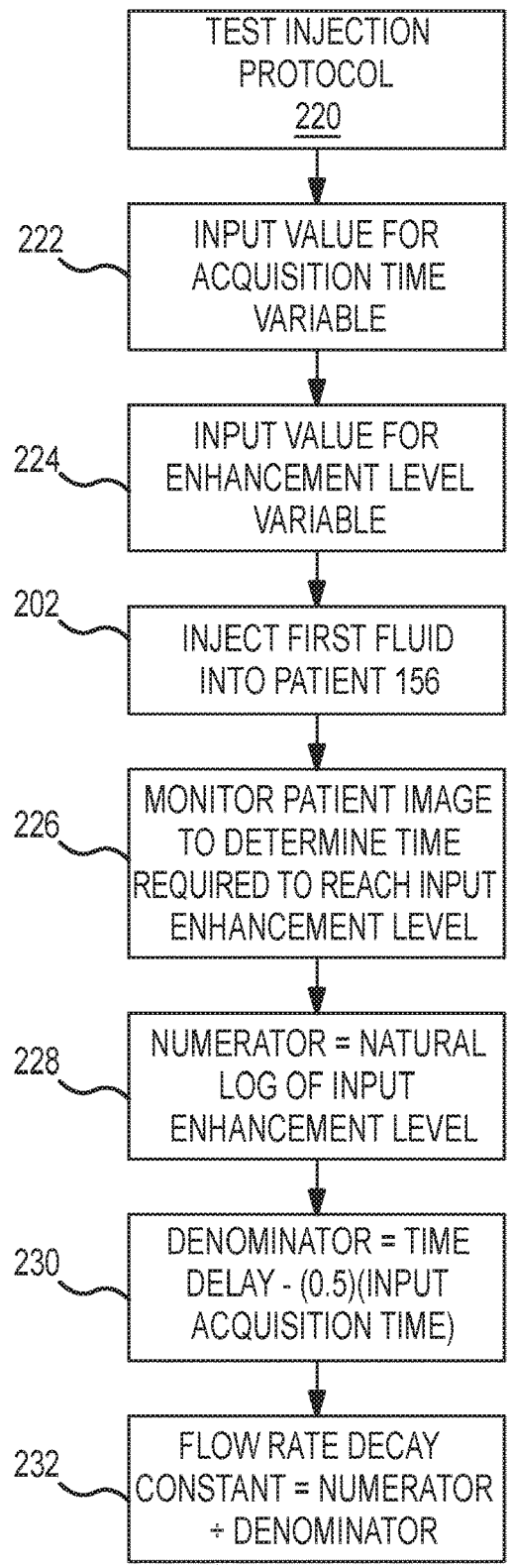
FIG. 9 is one embodiment of a test injection protocol that may be used by the medical imaging protocol of FIG. 8.

One embodiment of a test injection protocol for a heart imaging application (e.g., a computed tomography angiogram) is identified by reference numeral 220, is illustrated in FIG. 9, and may be used as the test injection protocol 194 for the power injector control logic 190 of FIG. 7. In one embodiment, the test injection protocol 220 may be used for purposes of steps 202, 204, and 206 of the medical imaging protocol 200 of FIG. 8. In any case, steps 222 and 224 of the test injection protocol 220 are data input steps, and may be executed in any order and in any appropriate manner. Step 222 is directed to inputting a value for an acquisition time variable. Any appropriate value may be used as the acquisition time variable for purposes of step 222. For instance, an operator may input a value for the acquisition time variable of step 222 based upon prior knowledge, for instance what has been determined to be an average acquisition time over imaging multiple patients 156 using the imaging unit 152 (FIG. 4) or a "norm." In one embodiment, it may be known that about five seconds is required to acquire a suitable image of the heart (e.g., about 5 heartbeats) using a particular imaging unit 152. Alternatively, the value for the acquisition time variable for step 222 of the medical imaging protocol 220 may be specific to the patient 156 that is to be imaged. With regard to this patient-specific option, the number of heartbeats required for the imaging unit 152 to acquire a suitable image of the heart of the patient 156 (e.g., an empirically known value) may be divided by the number of heartbeats of the patient 156 per unit of time (e.g., heartbeats per minute) to acquire a value for the acquisition time variable for step 222.

Step 224 of the test injection protocol 220 is directed to inputting a value for an enhancement level variable. The value for the enhancement level variable for step 224 may be expressed as a percentage, for instance a desired level of enhancement for the left side of the heart of the patient 156 in relation to the right side of the heart of the patient 156. A 50% value for the enhancement level variable of step 224 would be equated with the target enhancement level for the left side of the heart of the patient 156 being 50% of the enhancement level of the right side of the heart of the patient 156 during an imaging procedure (e.g., enhancement via a contrast media injection) for purposes of the test injection protocol 220. The enhancement level variable for step 224 may be at least generally about 50% in one embodiment, and may be at least generally about 25% in another embodiment.

The test injection protocol 220 of FIG. 9 uses the first fluid injection step 202 discussed above in relation to the medical imaging protocol 200 of FIG. 8. Step 226 of the test injection protocol 220 is directed to monitoring a patient image to determine the time required to reach the enhancement level input in step 224. This time for purposes of step 226 may be referred to as a "time delay" or "time delay variable." Any way of monitoring may be utilized for purposes of step 226. For instance, this monitoring step 226 may utilize obtaining an intensity measurement of the left side of the heart of the patient 156, as well as obtaining an intensity measurement of the right side of the heart of the patient. The time for purposes of step 226 would be the time that has elapsed from the start of the first fluid injection of step 202, until reaching the input enhancement level from step 224 on the left side of the heart of the patient 156.

A flow rate decay constant may be derived or calculated from data associated with steps 222, 224, and 226. In one embodiment the flow rate decay constant may be determined by the following equation:

$$D_c = \frac{LN\ EL}{TD - 0.5(AT)}$$

where "LN" is the natural logarithm, where EL is the input value for the enhancement level variable from step 224, where TD is the time determined in accordance with step 226, and where AT is the value for the acquisition time variable input in step 222. Step 228 is directed to calculating the numerator for the above-noted equation, step 230 is directed to calculating the denominator for the above-noted equation, and step 232 is directed to dividing the numerator (step 228) by the denominator (step 230) to determine the flow rate decay constant.

Each of the power injector control logic 160 (FIG. 5) and the power injector control logic 190 (FIG. 7) may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. Each of the power injector control logic 160 (FIG. 5) and the power injector control logic 190 (FIG. 7) may be implemented at any single location or at multiple locations that are interconnected in any appropriate manner (e.g., via any type of network).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector comprising:
a syringe plunger driver comprising a motorized drive source;
a syringe comprising a syringe plunger, wherein said syringe plunger driver interacts with said syringe plunger to move said syringe plunger within said syringe in at least in a first direction;
power injector control logic comprising an injection protocol, wherein said injection protocol comprises a flow rate decay constant, and wherein execution of said injection protocol by said power injector, using said power injector control logic, generates an exponentially decaying flow rate injection;
data storage accessible by said power injector control logic and comprising a plurality of data entries, wherein each data entry of said plurality of data entries comprises a flow rate decay constant value and an imaging device identifier, wherein a first data entry of said plurality of data entries comprises a first flow rate decay constant value and a first imaging device model, wherein a second data entry of said plurality of data entries comprises a second flow rate decay constant value and a second imaging device model, wherein said first flow rate decay constant value is different from said second flow rate decay constant value, wherein said first imaging device model is different from said second imaging device model, wherein said first flow rate decay constant value is used by said power injector to execute said injection protocol for a first imaging operation that uses power injector and said first imaging device model, and wherein said second flow rate decay constant value is used by said power injector to execute said injection protocol for a second imaging operation that uses said power injector and said second imaging device model; and
a user input device operable to identify one of said data entries from said plurality of data entries as a selected data entry, and wherein said flow rate decay constant value of said selected data entry is used as said flow rate decay constant for execution of said injection protocol by said power injector using said power injector control logic.

2. The power injector of claim 1, further comprising a graphical user interface.

3. The power injector of claim 2, further comprising a first output on said graphical user interface, wherein said first output comprises a listing of at least some of said plurality of data entries and an associated said flow rate decay constant value.

4. The power injector of claim 1, wherein said data storage comprises a data structure, which in turn comprises said plurality of data entries.

5. The power injector of claim 4, wherein said data structure is searchable based upon an imaging device identifier value that is input through said user input device.

6. The power injector of claim 4, wherein said data structure is searchable by using said user input device to enter a model for an imaging device.

7. The power injector of claim 4, wherein said data structure is searchable by using said user input device to enter a model number for an imaging device.

8. The power injector of claim 1, wherein said imaging device identifier for each said data entry of said plurality of data entries comprises a model.

9. The power injector of claim 1, wherein said imaging device identifier for each said data entry of said plurality of data entries comprises a model number.

10. The power injector of claim 1, wherein said power injector is configured to accommodate searching of said data storage.

11. A power injector comprising:
a syringe plunger driver comprising a motorized drive source;
a syringe comprising a syringe plunger, wherein said syringe plunger driver interacts with said syringe plunger to move said syringe plunger within said syringe in at least in a first direction;
power injector control logic comprising an injection protocol, wherein said injection protocol comprises a flow rate decay constant, and wherein execution of said injection protocol by said power injector, using said power injector control logic, generates an exponentially decaying flow rate injection; and
data storage accessible by said power injector control logic and comprising a plurality of data entries, wherein each data entry of said plurality of data entries comprises a flow rate decay constant value and an imaging device identifier, wherein a first data entry of said plurality of data entries comprises a first flow rate decay constant value and a first imaging device model, wherein a second data entry of said plurality of data entries comprises a second flow rate decay constant value and a second imaging device model, wherein said first flow rate decay constant value is different from said second flow rate decay constant value, wherein said first imaging device model is different from said second imaging device model, wherein said first flow rate decay constant value is used by said power injector to execute said injection protocol for a first imaging operation that uses said power injector and said first imaging device model, and wherein said second flow rate decay constant value is used by said power injector to execute said injection protocol for a second imaging operation that uses said power injector and said second imaging device model.

12. The power injector of claim 11, further comprising a graphical user interface.

13. The power injector of claim 12, further comprising a first output on said graphical user interface, wherein said first output comprises a listing of at least some of said plurality of data entries and an associated said flow rate decay constant value.

14. The power injector of claim 11, wherein said data storage comprises a data structure, which in turn comprises said plurality of data entries.

15. The power injector of claim 14, wherein said data structure is searchable based upon an imaging device identifier value that is input through said graphical user interface.

16. The power injector of claim 14, wherein said data structure is searchable by a model for an imaging device.

17. The power injector of claim 14, wherein said data structure is searchable by a model number for an imaging device.

18. The power injector of claim 11, wherein said imaging device identifier for each said data entry of said plurality of data entries comprises a model number.

19. The power injector of claim 11, wherein said power injector is configured to accommodate searching of said data storage.

\* \* \* \* \*